(12) United States Patent
Tappel (10) Patent No.: US 7,005,636 B2
(45) Date of Patent: Feb. 28, 2006

(54) METHOD AND APPARATUS FOR MANIPULATING A MICROSCOPIC SAMPLE

(75) Inventor: Hendrik Gezinus Tappel, Casteren (NL)

(73) Assignee: FEI Company, Hillsboro, OR (US)

( * ) Notice: Subject to any disclaimer, the term of this patent is extended or adjusted under 35 U.S.C. 154(b) by 58 days.

(21) Appl. No.: 10/863,547

(22) Filed: Jun. 8, 2004

(65) Prior Publication Data

US 2004/0251412 A1  Dec. 16, 2004

(30) Foreign Application Priority Data

Jun. 13, 2003 (NL) .................................... 1023657
Feb. 17, 2004 (NL) .................................... 1025503

(51) Int. Cl.
*G01N 1/28* (2006.01)

(52) U.S. Cl. .............. 250/304; 250/492.21; 250/492.2; 250/492.1; 250/309

(58) Field of Classification Search ................ 250/309, 250/492.21, 492.1, 492.2, 304
See application file for complete search history.

(56) References Cited

U.S. PATENT DOCUMENTS

| | | | |
|---|---|---|---|
| 5,270,552 A | | 12/1993 | Ohnishi et al. |
| 6,420,722 B1 * | | 7/2002 | Moore et al. .......... 250/559.27 |
| 6,570,170 B1 * | | 5/2003 | Moore .................... 250/492.21 |
| 6,781,125 B1 | | 8/2004 | Tokuda et al. |
| 2004/0178355 A1 | | 9/2004 | Rasmussen |
| 2004/0178372 A1 | | 9/2004 | Rasmussen |
| 2004/0256555 A1 * | | 12/2004 | Shichi et al. ............... 250/307 |

FOREIGN PATENT DOCUMENTS

JP  2001272316  5/2001

* cited by examiner

*Primary Examiner*—John R. Lee
*Assistant Examiner*—Johnnie L Smith, II
(74) *Attorney, Agent, or Firm*—Michael O. Scheinberg

(57) ABSTRACT

In the semiconductor industry, microscopic samples are cut out of substrates for purposes of analysis. In the case of a known method, a sample to be cut loose out of a substrate is attached to a sample carrier connected to a manipulator and the sample is cut loose from the substrate. Subsequently, the sample is fixed to a TEM grid and completely separated from the sample carrier.

According to the invention, the sample carrier 3 is left in connection with the sample 1 and the sample carrier 3 is separated from the manipulator 4. By making the sample carrier 3 connected to the sample 1 much bigger than the (microscopic) sample 1, and by manipulating the sample carrier 3, manipulation—with the aid of a (macroscopic) manipulator—of the microscopic sample 1 attached thereto becomes easier than manipulating the sample 1 without the sample carrier 3 attached thereto. In addition, a mechanical coupling between manipulator 4 and sample carrier 3 is shown, which enables a great degree of automation.

22 Claims, 6 Drawing Sheets

METHOD AND APPARATUS FOR MANIPULATING A MICROSCOPIC SAMPLE

The invention relates to a method of manipulating a microscopic sample to be extracted from a substrate, whereby the manipulating movements are conducted with the aid of a manipulation system consisting of a sample carrier and a manipulator, which method comprises the following steps:

attaching the sample to the sample carrier and completely severing the sample from the substrate, and;

subsequently applying a separation to the sample and the manipulator.

The invention also relates to a particle-optical apparatus for performing this method.

Such a method is known from U.S. Pat. No. 6,420,722 B2.

Such methods are principally used in the semiconductor industry, where samples of microscopic dimensions are removed from substrates such as wafers so as to make analyses and/or processing steps possible. Nowadays, such samples have dimensions of the order of magnitude of 10 $\mu$m at a thickness of 100 $\mu$m. There is a tendency towards still further miniaturization of the structures of interest, and an attendant miniaturization of the samples to be extracted. The analyses can, for example, be conducted with the aid of a TEM (Transmission Electron Microscope), SEM (Scanning Electron Microscope), SIMS (Secondary Ion Mass Spectroscope) or X-ray analytical apparatus. The further processing steps may, for example, comprise thinning the sample with the aid of an ion beam as part of an analysis with the aid of a TEM.

In the case of the method described in the cited patent text, a sample carrier in the form of a needle is moved on a manipulator to a position on a substrate where a sample is to be extracted from a substrate. Before completely severing the sample from the substrate, the sample is attached to the extremity of the needle-shaped sample carrier by means of metal deposition.

In U.S. Pat. No. 6,570,170, an alternative method is described for removing a sample from a wafer and attaching it to a sample carrier. To this end, the sample is first cut completely loose from the substrate using a particle beam and is then attached to the sample carrier. In the case of both known methods, a situation is achieved whereby the sample is cut loose from the substrate and attached to the sample holder so that the sample can be manipulated with the aid of the sample holder.

After completely cutting the sample loose with the aid of a particle beam, the sample attached to the manipulator is brought to another position with the aid of the manipulator.

The sample is subsequently fixed to a carrier in the form of a TEM grid with the aid of metal deposition. The TEM grid has hollows and the sample is attached to the edge of such a hollow. After affixing the sample to the TEM grid, the separation between the manipulator and the sample is applied by employing an ion beam to cut loose the metal deposition connection between the sample and manipulator.

A TEM grid consists of a metal foil in which hollows are created that are bordered by bars of said metal. It usually has an external diameter of the order of magnitude of 3 mm, hollows of 15 $\mu$m or larger, bordered by bars with a width of 10 $\mu$m or more and a thickness of 10 $\mu$m or more. Depending on the chosen embodiment of a TEM grid, the hollows may be up to hundreds of $\mu$m in size.

A disadvantage of the known method is that the sample mounted on the sample carrier has to be positioned with sub-micron accuracy on the TEM grid by the manipulation system, so as to connect the corner points of the sample to the edge of the hollow without hindering the spatial accessibility of the sample during further processing and/or analysis. In this respect, it is important to realize that the sample has a size comparable to or smaller than the width of the bars of the TEM grid.

Another disadvantage of the described method is that it does not offer the possibility of processing or analyzing the sample in apparatus that requires another grid or holder than that on which the sample is affixed.

A further disadvantage lies in the determination of the position of the sample on the TEM grid, whereby, somewhere on the TEM grid—with a size of the order of magnitude of 3 mm and with hundreds of hollows—the microscopic sample—with a size of the order of magnitude of 10 $\mu$m—is fixed to a bar.

The invention aims to provide a method that better facilitates manipulation of the microscopic sample.

To this end, a method according to the invention is characterized in that the separation is applied between the manipulator and the sample carrier in such a manner that, after applying the separation, a portion of the sample carrier that protrudes with respect to the sample remains attached to the sample.

By making the sample carrier substantially larger than the microscopic sample and by manipulating the sample carrier, manipulation—with the aid of a macroscopic manipulator—of the microscopic sample attached thereto becomes easier than manipulating the sample without the sample carrier attached thereto.

When mounting the sample on a TEM grid, with hollows much bigger than the sample, one achieves a substantial reduction in the necessary positioning accuracy, and an attendant increase in the ease of manipulation, if the sample carrier is manipulated in such a manner that the sample is located in its entirety within a hollow and the sample carrier thereby rests on one or more bars of the TEM grid.

Remounting of the sample can occur by release, manipulation and mounting of the sample carrier, which is easier and more effective than release, manipulation and mounting of the microscopic sample. Such remounting may be necessary so as to change the position or orientation of the sample in the case of initially erroneous placement, or so as to mount the sample on another grid or another holder for use in apparatus in which the sample is to undergo subsequent processing or analysis.

Finally, positional determination of the microscopic sample attached to the (relatively large) sample carrier is easier than positional determination of the sample without sample carrier: one first determines the position of the sample carrier and one then localizes the sample attached thereto by following the form of the sample carrier.

In a preferential embodiment of the method according to the invention, the sample carrier has a rod-like extremity and the location where the sample is attached to the sample carrier is an extremity of the sample carrier. An advantage of this embodiment is that visibility at the location where the extremity of the relatively large sample carrier is attached to the microscopic sample is blocked as little as possible by the sample carrier itself, as a result of which the positioning of the extremity of the sample carrier upon the sample to be removed, before the sample is cut loose, is made as simple as possible.

In a further embodiment of the method according to the invention, the sample carrier is formed by an end portion of a supply of wire, and, in this scenario, the separation is applied by separating the end portion of the supply of wire from the supply of wire. An attendant advantage of this embodiment is that the remaining end of the supply of wire can—in the case of repeated application of the method—now be used as a new end portion of a subsequent sample carrier. In this scenario, separation can comprise stretching the wire of the supply of wire in such a manner that constriction of the wire occurs, which has the advantage that the newly formed end of the supply of wire has a smaller diameter than the rest of the sample carrier, which simplifies placement of that end upon the microscopic sample to be removed.

In another embodiment of the method according to the invention, the sample carrier is detachably coupled to the manipulator. An advantage of this embodiment is that the manipulator—in an automated manner, and thus without human intervention—can remove the sample carrier from, for example, a cassette and, after attachment of the sample to the sample carrier and cutting loose of the sample, can place and release the sample carrier with attached sample into the same or another cassette, after which this cassette can be removed from the apparatus in which this method is performed, so as to allow the samples present in the cassette to undergo processing and/or analyses. The sample carrier can have a form that is suitable for use in apparatus for performing analyses and/or processing subsequent to extraction of the sample. The sample carrier can be embodied to hold multiple samples, which can shorten the time necessary for analysis and/or processing. It is also possible to provide the sample carrier with a unique identification code, which simplifies identification of the sample during subsequent analyses and/or processing. This embodiment of the apparatus is principally advantageous in environments where large numbers of samples are analyzed, such as in production environments for integrated circuits.

The invention will be elucidated on the basis of figures, in which identical reference symbols indicate corresponding elements.

Although the figures only explain the method by means of which the sample carrier is attached to the sample before the sample is cut loose from the substrate, it is just as possible to first cut the sample fully loose before attaching the sample to the sample carrier.

To this end.

Figure 1A:
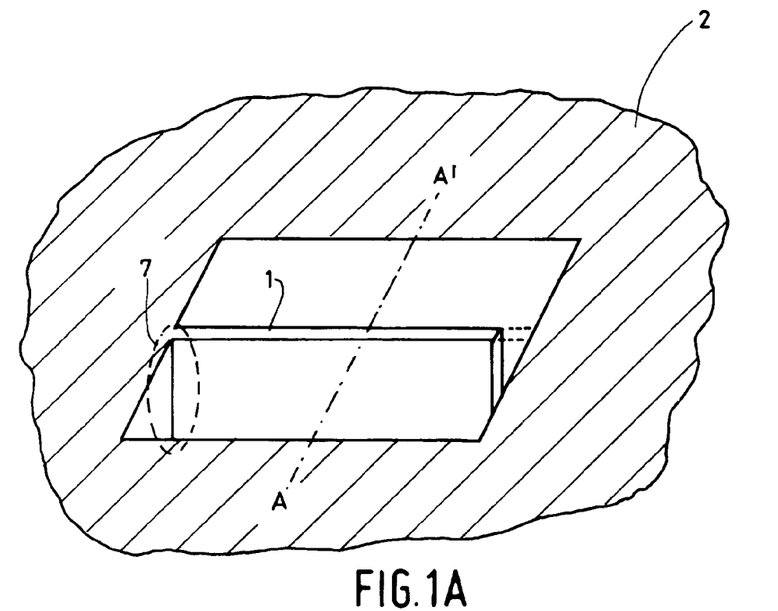
FIG. 1A is a schematic depiction of a wafer with a sample that is partially cut loose.
Figure 1B:
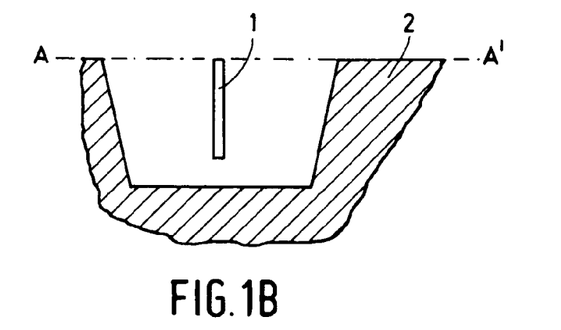
FIG. 1B is a schematic depiction of a transverse cross-section from FIG. 1A of the wafer with the partially cut loose sample.

FIGS. 1A and 1B show a substrate 2 in the form of a wafer containing a partially cut loose sample 1. The cutting loose of the sample can occur in a known manner with an ion beam. The underside of the sample 1 is already cut loose, and the sample is only connected to the wafer 2 via the connection 7 between wafer 2 and sample 1. The sample 1 nowadays has dimensions of the order of magnitude of 10 $\mu$m (i.e. length perpendicular to the line AA') at a thickness (i.e. dimension in the direction of the line AA') of 100 nm. The wafer 2 nowadays has a diameter of 300 mm, and it should be possible to take the sample from any random location on the wafer. FIG. 1B shows a transverse cross-section according to the line AA' depicted in FIG. 1A, in which it can clearly be seen that the underside of sample 1 is free from the wafer 2.

Figure 2:
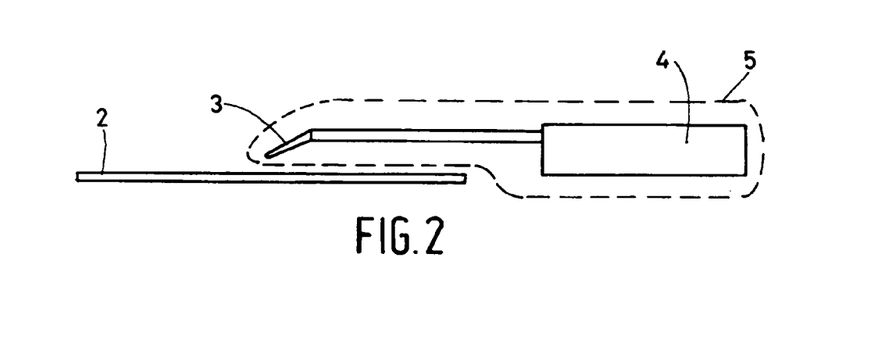
FIG. 2 is a schematic depiction of a manipulator system with a wafer.

FIG. 2 schematically shows a manipulator system 5, consisting of a manipulator 4 and a sample carrier 3. The manipulator 4 is able to move the sample carrier 3 within the plane of the wafer 2 to the position of the sample 1 to be removed from the wafer 2 (see FIG. 1A) and also perpendicular thereto. In view of the dimensions of the sample 1, this will have to occur with an accuracy of the order of magnitude of 1 $\mu$m. Manipulators for positioning wafers with this type of accuracy are known per se.

Figure 3:
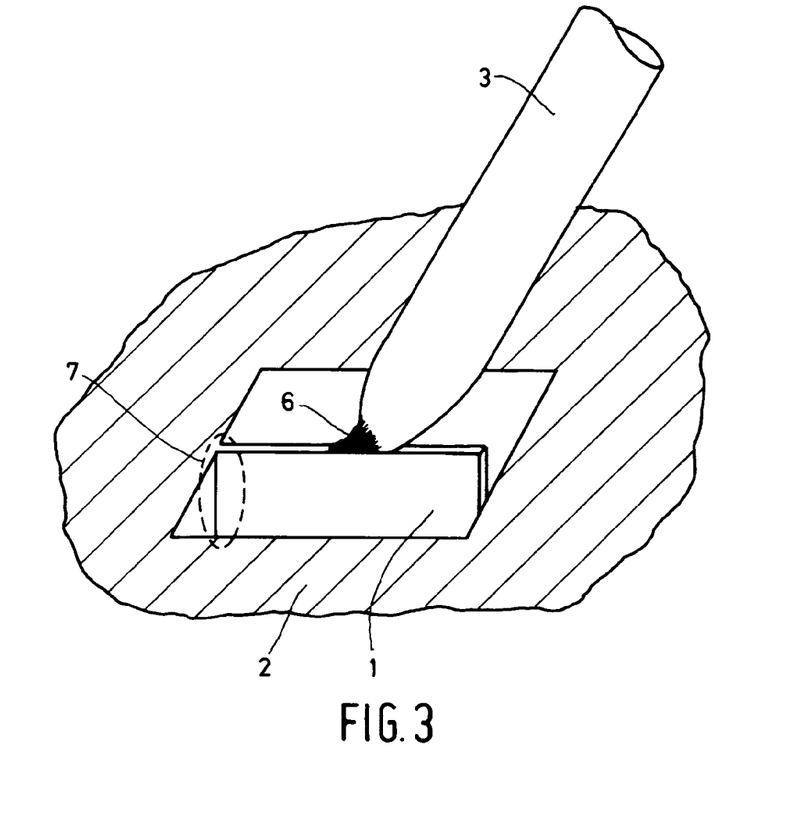
FIG. 3 is a schematic depiction of a wafer with a partially cut loose sample to which a sample carrier is attached.

FIG. 3 schematically shows an extremity of the sample carrier 3 (see FIG. 2), which is connected to the manipulator 4 (see FIG. 2) and which is attached to the sample 1, whereby the connection 6 is embodied in the form of a metal deposition. After cutting loose the connection 7 between the sample 1 and the wafer 2 with a particle beam, the sample 1 is only carried by the sample carrier 3.

Figure 4:
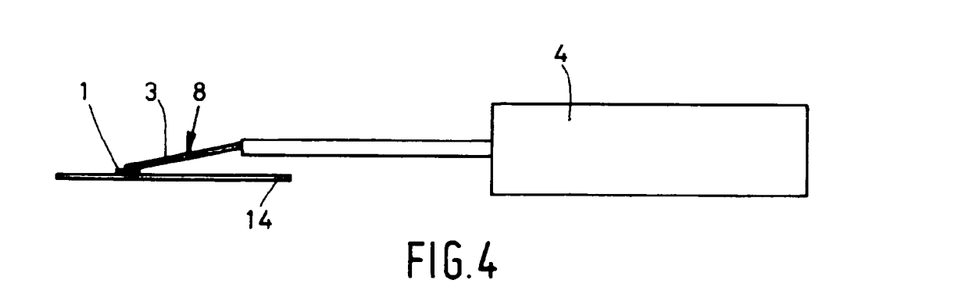
FIG. 4 is a schematic depiction of a manipulator system with a sample attached thereto in which the cutting loose of sample carrier and manipulator is occurring.

FIG. 4 schematically shows the manipulator 4, which is positioning the sample carrier 3 (connected thereto)—and the sample 1 attached thereto—above a TEM grid 14. The sample carrier 3 is positioned above the TEM grid 14 by the manipulator 4 in such a manner that the sample 1, after separation, is located entirely within one of the hollows of the TEM grid 14 and the sample carrier 3 comes to rest upon one or more of the bars of the TEM grid 14, such as is further depicted in FIG. 5. Subsequently—using, for example, a laser or particle beam—a separation is applied between the manipulator 4 and the sample carrier 3 at a position 8, whereby the portion of the sample carrier 3 that protrudes with respect to the sample 1 and that remains connected to the sample 1 is large with respect to the sample 1.

Figure 5:
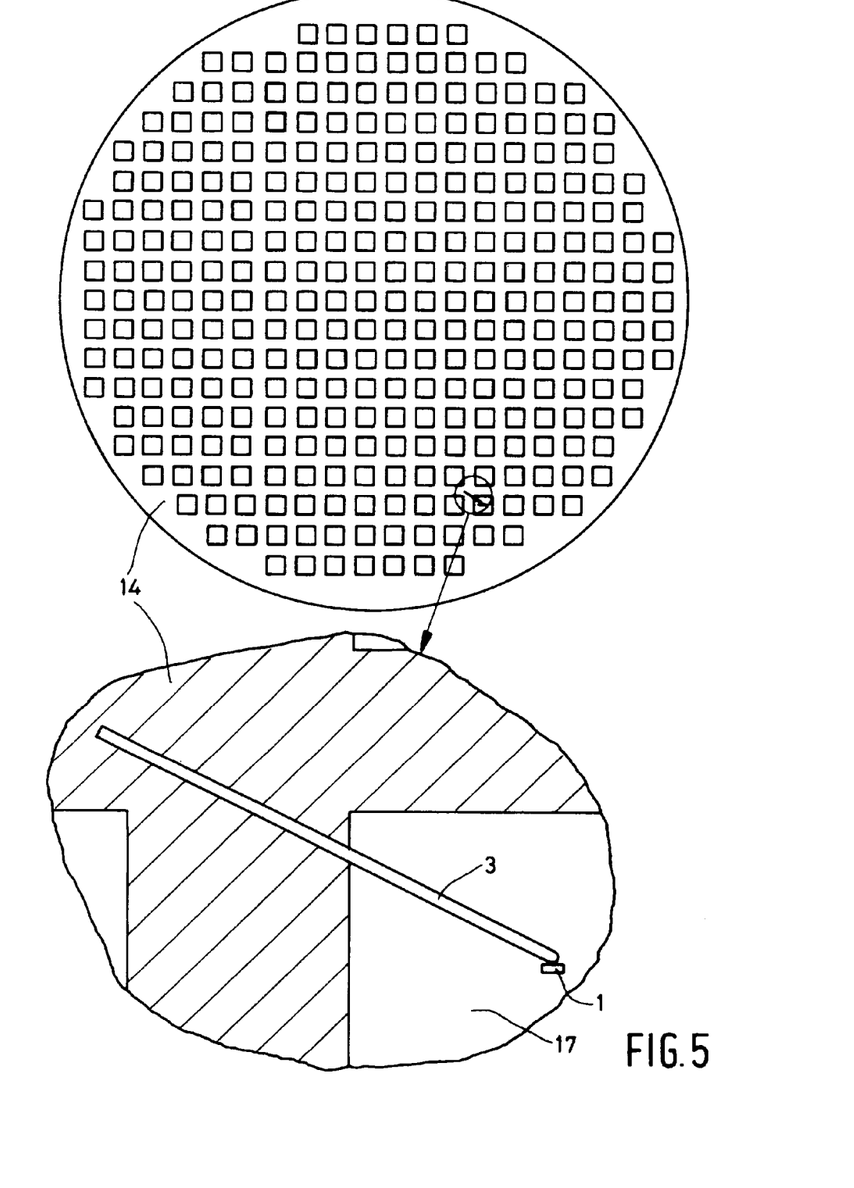
FIG. 5 is a schematic depiction of a TEM grid upon which is located the sample carrier with sample attached thereto.

FIG. 5 schematically shows the positioning of the sample 1 after a separation has been applied between the sample carrier 3 and the manipulator 4. The sample carrier 3 rests upon one bar of the TEM grid 14 and the sample 1 is located entirely within a hollow 17 of the TEM grid 14, as a result of which the sample 1 is easily accessible for the purpose of processing and/or analysis in other apparatus.

Figure 6:
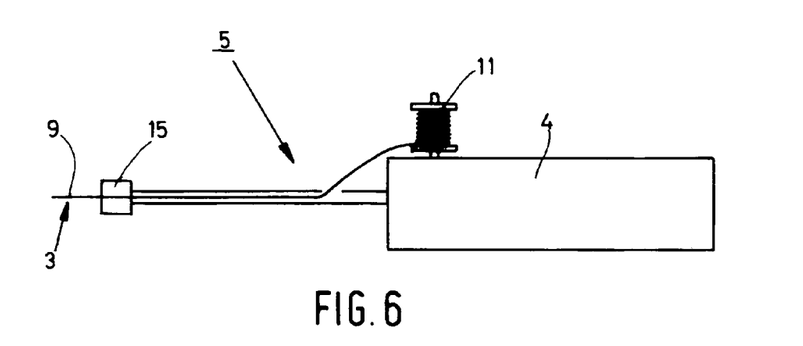
FIG. 6 is a schematic depiction of a manipulator system in which the sample carrier is formed by a supply of wire.

FIG. 6 schematically shows an embodiment of the manipulator system 5, whereby the sample carrier 3 (see FIG. 2) is formed by the end portion 9 of a supply 11 of wire. In addition, separation means 15 are schematically shown here, which means 15 may be mechanical in nature—as will be explained further in FIG. 7—but which may also be embodied as severing means that perform the separation with the aid of a laser or particle beam. Use of the supply 11 of wire makes it possible, in the case of repeated application of the method, to produce sample carriers 3 in a simple manner. The sample carrier 3, and thus the wire from which the sample carrier 3 is formed, should be very thin, in view of the dimensions of the sample 1 upon which the sample carrier 3 is positioned. In this context, one might consider wire such as that used in the semiconductor industry for "bonding" chips, which wire can have a diameter nowadays of 10 μm.

Figure 7A:
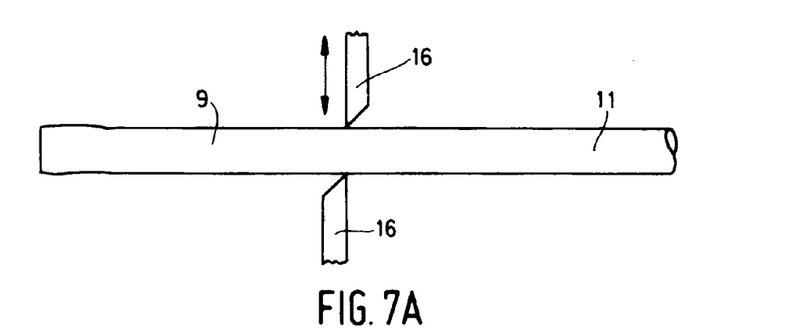
FIG. 7A is a schematic depiction of mechanical separation means such as can be used in FIG. 6.

FIG. 7A schematically shows an embodiment of the mechanical separation means referred to with regard to FIG. 6, whereby the end portion 9 is mechanically severed from the supply 11 of wire using knives 16 operating toward one another.

Figure 7B:
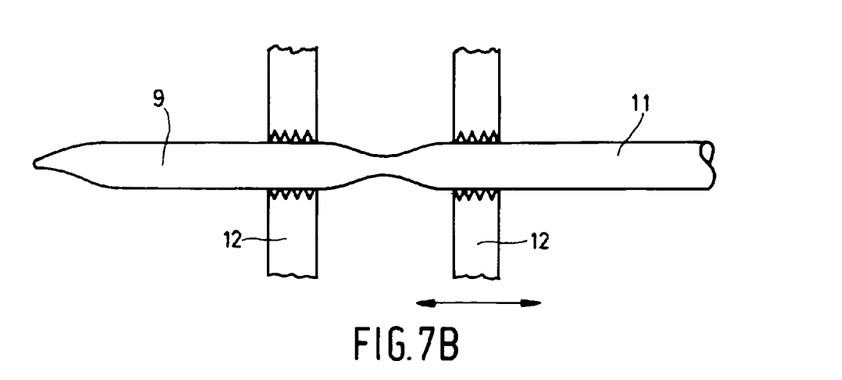
FIG. 7B is a schematic depiction of mechanical separation means such as can be used in FIG. 6.

FIG. 7B schematically shows an embodiment of the mechanical separation means referred to with regard to FIG. 6, whereby the end portion 9 is mechanically severed from the supply 11 of wire by means of stretching of the supply 11 of wire, achieved by moving apart the clamps 12, as a result of which constriction of the wire of the supply 11 of wire occurs. The constriction will have a diameter much smaller than the diameter of the end portion 9, so that the needle-like extremity of the end portion 9 to be newly formed as a result of this constriction will also be much thinner than the diameter of the wire of the supply 11 of wire, so that positioning upon the microscopic sample 1 is facilitated.

Figure 8A:
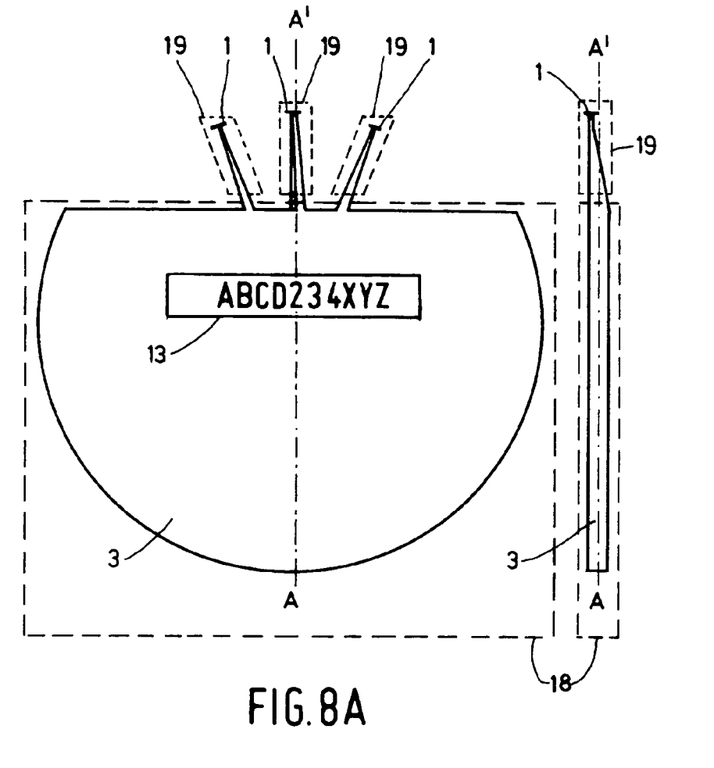
FIG. 8A depicts a detachable sample carrier.

FIG. 8 shows—in a front elevation and also in a transverse cross-section according to line AA'—a sample carrier 3 that can be detachably coupled to the manipulator 4 already shown in FIG. 2. In the figure, it can be seen that the sample carrier 3 is formed from a relatively thick body 18, which the manipulator 4 can grip for the purpose of coupling, and tapering fingers 19 for attachment of samples 1. The form of the sample carrier 3 is chosen in such a manner that it is possible to use it in standard specimen carriers in apparatus in which processing and/or analysis are performed. These may be specimen carriers for use with TEM grids for application in TEM apparatus. The sample carrier 3 is embodied to carry several samples 1, thanks to the presence of several fingers 19. As a result of the form, placement and direction of the fingers 19, one achieves a situation whereby a sample 1 can be attached to the extremity of one of the fingers 19 without the risk that a sample 1 that is already attached to another finger 19 will come into contact with the wafer 2, seeing as such contact could damage the sample 1 that is already attached, or could damage the connection between the sample carrier 3 and the sample 1 that is already attached. In addition, sample carrier 3 is provided with a (unique) identification code 13, which, during subsequent analyses and/or processing, facilitates identification of the samples attached to the sample carrier 3. This identification is of particular advantage in environments in which large numbers of samples are analyzed, such as in environments for the production of integrated circuits.

Figure 8B:
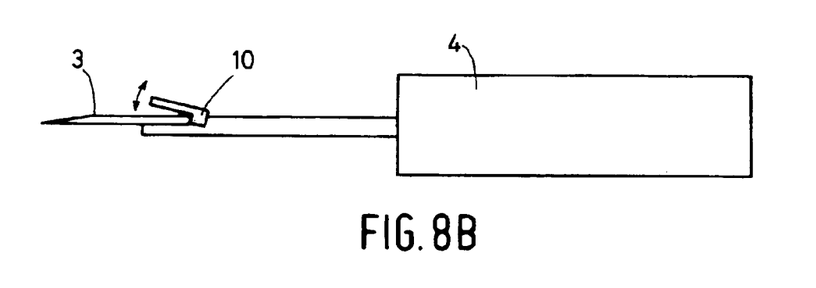
FIG. 8B depicts a manipulator with mechanical holding means for manipulating a sample carrier as shown in FIG. 8A.

FIG. 8B schematically shows a sample carrier 3 such as shown in FIG. 8A, which is coupled to a manipulator 4 with the aid of a coupling mechanism 10, which coupling mechanism 10 is part of the manipulator 4. The mouth of this coupling mechanism 10 is closed using an actuator that is not depicted, whereby the sample carrier 3 becomes clamped.

Figure 9:
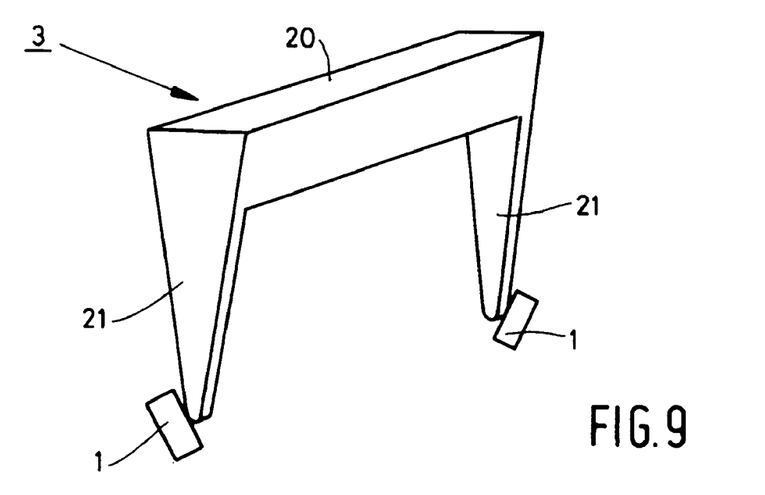
FIG. 9 depicts a detachable sample carrier embodied for attachment to a flat holder.
Figure 10:
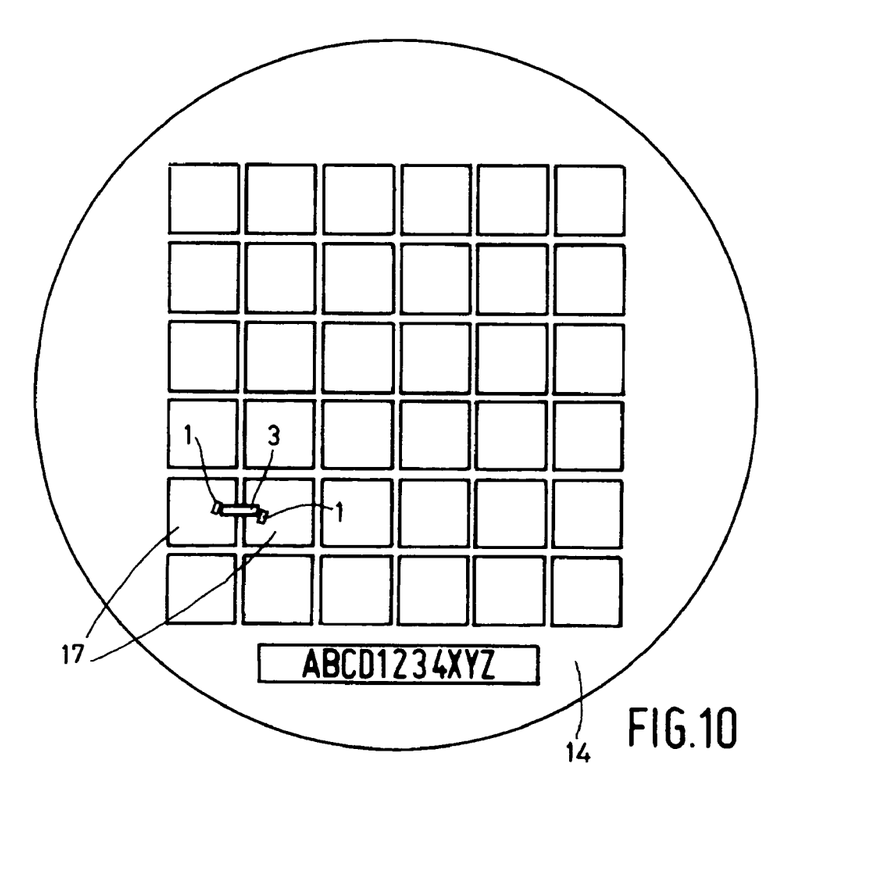
FIG. 10 shows a flat holder to which the sample carrier of FIG. 9 is attached.

FIG. 9 schematically shows another embodiment of a detachable sample carrier 3, which, in turn, is attached to a flat holder with one or more hollows 17—such as is further depicted in FIG. 10. This sample carrier 3 has a U form with a relatively thick middle portion 20 and thin legs 21. The relatively thick middle portion 20 can be gripped by a coupling mechanism 10 such as that shown in FIG. 8B. The sample 1 is attached to the thin legs 21.

FIG. 10 schematically shows the sample carrier 3 such as shown in FIG. 9 attached to a flat holder in the form of a TEM grid 14 with hollows 17, whereby the samples 1 connected to the sample carrier 3 both lie freely within a hollow 17. In addition, the TEM grid 14 is provided with a unique identification code 13.

What is claimed is:

1. A method of manipulating a microscopic sample to be extracted from a substrate, whereby the manipulating movements are conducted with the aid of a manipulation system consisting of a sample carrier and a manipulator, which method comprises the following steps:
   attaching the sample to the sample carrier and completely severing the sample from the substrate, and;
   subsequently applying a separation to the sample and the manipulator,
characterized in that the separation is applied between the manipulator and the sample carrier in such a manner that, after applying the separation, a portion of the sample carrier that protrudes with respect to the sample remains attached to the sample.

2. A method according to claim 1, whereby the sample carrier has a rod-like extremity and the location where the sample is attached to the sample carrier is the rod-like extremity of the sample carrier.

3. A method according to claim 1, whereby the sample carrier is formed by an end portion of a supply of wire, and whereby the separation is applied by separating the end portion of the supply of wire from the supply of wire.

4. A method according to claim 3, whereby the method comprises stretching the wire of the supply of wire, at the location of the separation area where the separation is to occur, in such a manner that constriction of the wire occurs.

5. A method according to claim 1, whereby the sample carrier is detachably coupled to the manipulator.

6. A method according to claim 5, whereby the sample carrier is embodied to carry several samples.

7. A method according to claim 5, whereby the sample carrier is provided with a unique identification code.

8. A method according to claim 5, whereby the sample carrier is attached to a flat holder with a hollow in such a manner that the sample is located within the hollow so as to be substantially free all around.

9. A method according to claim 8, whereby attachment of the sample carrier to the flat holder occurs by mechanical clamping.

10. A method according to claim 8, whereby the flat holder is provided with a unique identification code.

11. A particle-optical apparatus for performing the method according to claim 3, provided with:
   a particle source for producing a particle beam to cut a sample loose out of a substrate;
   a manipulator for moving a sample carrier to a position on a substrate where the sample is to be extracted from the substrate,
characterized in that the particle-optical device is provided with a supply of wire for the purpose of forming a sample carrier and that the particle-optical apparatus is provided with severing means for applying a separation between the supply of wire and an end portion of the supply of wire for the purpose of obtaining the sample carrier.

12. Particle-optical apparatus for performing the method according to claim 5, provided with:

a particle source for producing a particle beam to cut a sample loose out of a substrate;

a manipulator for moving a sample carrier to a position on a substrate where the sample is to be extracted from the substrate, characterized in that the manipulator comprises a coupling mechanism for detachably attaching the sample carrier to the manipulator.

13. A method according to claim 2, whereby the sample carrier is formed by an end portion of a supply of wire, and whereby the separation is applied by separating the end portion of the supply of wire from the supply of wire.

14. A method according to claim 13, whereby the method comprises stretching the wire of the supply of wire, at the location of the separation area where the separation is to occur, in such a manner that constriction of the wire occurs.

15. A method according to claim 2, whereby the sample carrier is detachably coupled to the manipulator.

16. A method according to claim 15, whereby the sample carrier is embodied to carry several samples.

17. A method according to claim 15, whereby the sample carrier is attached to a flat holder with a hollow in such a manner that the sample is located within the hollow so as to be substantially free all around.

18. A method according to claim 16, whereby the sample carrier is attached to a flat holder with a hollow in such a manner that the sample is located within the hollow so as to be substantially free all around.

19. A method according to claim 9, whereby the flat holder is provided with a unique identification code.

20. A particle-optical apparatus for performing the method according to claim 4, provided with:

a particle source for producing a particle beam to cut a sample loose out of a substrate;

a manipulator for moving a sample carrier to a position on a substrate where the sample is to be extracted from the substrate, characterized in that the particle-optical device is provided with a supply of wire for the purpose of forming a sample carrier and that the particle-optical apparatus is provided with severing means for applying a separation between the supply of wire and an end portion of the supply of wire for the purpose of obtaining the sample carrier.

21. Particle-optical apparatus for performing the method according to claim 8, provided with:

a particle source for producing a particle beam to cut a sample loose out of a substrate;

a manipulator for moving a sample carrier to a position on a substrate where the sample is to be extracted from the substrate, characterized in that the manipulator comprises a coupling mechanism for detachably attaching the sample carrier to the manipulator.

22. Particle-optical apparatus for performing the method according to claim 15, provided with:

a particle source for producing a particle beam to cut a sample loose out of a substrate;

a manipulator for moving a sample carrier to a position on a substrate where the sample is to be extracted from the substrate, characterized in that the manipulator comprises a coupling mechanism for detachably attaching the sample carrier to the manipulator.

* * * * *